US009487836B2

(12) United States Patent
Hooper

(10) Patent No.: US 9,487,836 B2
(45) Date of Patent: Nov. 8, 2016

(54) METHODS AND COMPOSITIONS FOR IDENTIFYING YEAST

(71) Applicant: Medical Service Consultation International, LLC, Dallas, TX (US)

(72) Inventor: Dennis G. Hooper, Lewisville, TX (US)

(73) Assignee: Medical Service Consultation International, LLC, Carrollton, TX (US)

(*) Notice: Subject to any disclaimer, the term of this patent is extended or adjusted under 35 U.S.C. 154(b) by 108 days.

(21) Appl. No.: 14/605,720

(22) Filed: Jan. 26, 2015

(65) Prior Publication Data

US 2015/0176087 A1 Jun. 25, 2015

Related U.S. Application Data

(63) Continuation of application No. 12/545,732, filed on Aug. 21, 2009, now abandoned.

(60) Provisional application No. 61/091,188, filed on Aug. 22, 2008.

(51) Int. Cl.
C12P 19/34 (2006.01)
C12Q 1/68 (2006.01)
G01N 33/569 (2006.01)

(52) U.S. Cl.
CPC ....... *C12Q 1/6895* (2013.01); *G01N 33/56961* (2013.01); *C12Q 2600/158* (2013.01)

(58) Field of Classification Search
CPC .......... C12Q 1/6895; C12Q 2600/158; G01N 33/56961
USPC ....................................................... 435/91.2
See application file for complete search history.

(56) References Cited

U.S. PATENT DOCUMENTS

| | | | |
|---|---|---|---|
| 4,683,202 A | 7/1987 | Mullis | |
| 4,744,981 A | 5/1988 | Pavanasasivam | |
| 4,772,551 A | 9/1988 | Hart et al. | |
| 4,800,159 A | 1/1989 | Mullis et al. | |
| 4,906,452 A | 3/1990 | Sivam | |
| 5,261,394 A | 11/1993 | Mulligan et al. | |
| 5,426,027 A | 6/1995 | Lott et al. | |
| 5,707,802 A * | 1/1998 | Sandhu .................. | C07K 14/37 435/270 |
| 5,776,694 A | 7/1998 | Sheiness et al. | |
| 6,210,345 B1 | 4/2001 | Van Brunt | |
| 6,268,222 B1 | 7/2001 | Chandler et al. | |
| 6,345,025 B1 | 2/2002 | Yamamiya | |
| 6,362,008 B1 | 3/2002 | Kohn et al. | |
| 6,372,430 B1 | 4/2002 | Morrison et al. | |
| 6,696,304 B1 | 2/2004 | Davies | |
| 6,699,670 B2 | 3/2004 | Rothman et al. | |
| 6,846,631 B2 | 1/2005 | Beck et al. | |
| 6,872,523 B1 | 3/2005 | Iwen et al. | |
| 7,384,622 B2 | 6/2008 | Hata et al. | |
| 8,628,928 B2 | 1/2014 | Hooper | |
| 8,956,821 B2 | 2/2015 | Hooper | |
| 8,962,251 B2 | 2/2015 | Hooper | |
| 2001/0004813 A1 | 6/2001 | Hedman | |
| 2003/0054356 A1 | 3/2003 | Jacobson et al. | |
| 2003/0129600 A1 | 7/2003 | Morrison et al. | |
| 2003/0203412 A1 | 10/2003 | Vojdani | |
| 2004/0023207 A1 | 2/2004 | Polansky | |
| 2004/0170981 A1 | 9/2004 | McKenney et al. | |
| 2005/0176023 A1 | 8/2005 | Ramon et al. | |
| 2008/0014582 A1 | 1/2008 | Hooper | |
| 2008/0108905 A1 | 5/2008 | Lurie | |
| 2010/0068718 A1 | 3/2010 | Hooper | |
| 2010/0075322 A1 | 3/2010 | Hooper | |
| 2010/0129821 A1 | 5/2010 | Fredricks | |
| 2011/0104684 A1 | 5/2011 | Hooper | |
| 2013/0059307 A1 | 3/2013 | Hooper | |
| 2013/0183697 A1 | 7/2013 | Hooper | |
| 2014/0221504 A1 | 8/2014 | Hooper | |
| 2014/0342927 A1 | 11/2014 | Hooper | |

FOREIGN PATENT DOCUMENTS

| | | |
|---|---|---|
| EP | 1215282 | 6/2002 |
| WO | WO96/21741 | 7/1996 |

(Continued)

OTHER PUBLICATIONS

Koster et al, "A geographically diverse set of isolates indicates two phylogenetic lineages within Strachybotrys Chartarum," Can. J. Bot., 2003; 81: 633-643.
Niesters et al, "Rapid, polymerase chain reaction-based identification assays for *Candida* species," Journal of Clinical Microbiology, 1993, 904-910.
Chen et al, "Identification of medically important yeases using PCR-based detection of DNA sequence polymorphisms in the internal transcribed spacer 2 region of the rRNA genes," Journal of Clinical Microbiology, 2000; 2302-2310.
Henry et al., "Identification of *Apsergillus* species using internal transcribed spacer regions 1 and 2," Journal of Clinical Microbiology, 2000; 1510-1515.
Fontelo, "Detection of T-2 toxin by an improved radioimmunoassay," Applied and Environmental Microbiology, 1983; 45(2):640-643.

(Continued)

*Primary Examiner* — Cynthia B Wilder
(74) *Attorney, Agent, or Firm* — Barnes & Thornburg LLP

(57) ABSTRACT

The invention relates to a method of identifying a specific yeast species in patient tissue or body fluid. The method comprises the steps of extracting and recovering DNA of the yeast species from the patient tissue or body fluid, amplifying the DNA, hybridizing a probe to the DNA to specifically identify the yeast species, and specifically identifying the yeast species. The invention also relates to a method of identifying a yeast mycotoxin in patient tissue or body fluid. The method comprises the steps of extracting and recovering the yeast mycotoxin from the patient tissue or body fluid, contacting the yeast mycotoxin with an antibody directed against the yeast mycotoxin, and identifying the yeast mycotoxin. Both of these methods can be used to determine if a patient is at risk for or has developed a disease state related to a yeast infection, and to develop an effective treatment regimen for the patient.

19 Claims, No Drawings

(56) References Cited

FOREIGN PATENT DOCUMENTS

| WO | WO98/50584 | 11/1998 |
|---|---|---|
| WO | WO01/54653 | 8/2001 |
| WO | WO2004/054359 | 7/2004 |
| WO | WO2007/023461 | 3/2007 |
| WO | WO 2008/051285 | 5/2008 |

OTHER PUBLICATIONS

Brasel et al, "Detection of airborne Stachybotrys chartarum macrocyclic trichothecene mycotoxins on particulates smaller than conidia," Applied and Environmental Microbiology, 2005; 71:114-122.

Kierek-Jaszcuk et al., "Detection and quantification of the T-2 mycotoxin by ELISA utilizing toxin-specific polyclonal antibodies raised in chickens," Food and Agricultural Immunology, 1995; 7:243-252.

Groopman et al, "High-affinity monoclonal antibodies for aflatoxins and their application to solid-phase immunoassays," P.N.A.S., 1984; 81:7728-7731.

Vetro, Thesis: Development of sensitive immunodiagnostics for determination of toxic residues (mycotoxins, drugs) in biological fluids and animal feeds, 2002.

Lewis et al., "Detection of gliotoxin in experimental and human aspergillosis," *Infection and Immunity*; 2005; 73(1): 635-637.

Spiess et al., "Development of a LightCycler PCR assay for detection and qualification of Aspergillus fumigatus DNA in clinical samples from neutropenic patients," *Journal of Clinical Microbiology*, 2003; 41(5): 1811-1818.

Fox et al., "Detection of Aspergillus fumigatus mycotoxins: immunogen synthesis and immunoassay development," *Journal of Microbiological Methods*, 2004; 6+: 221-230.

Bialek et al., "PCR based identification and discrimination of agents of mucomycosis and aspergillosis in paraffin wax embedded tissue," *J. Clin. Pathol.*, 2005; 58:1180-1184.

Zorgani et al,., "Detection pyrogenic toxin of *Staphylococcus aureus* in sudden infant death syndrome," *FEMS Immunology and Medical Microbiology*, 1999; 25: 103-108.

Stack et al., "Nonribosomal peptide synthesis in Apergillus fumigates and other fungi," *Microbiology*, 2007; 153(5): 1297-1306.

Ferns, "Evaluation of the role of real-time PCR in the diagnosis of invasive aspergillosis," *Leukemia & Lymphoma*, 2006; 41(1): 15-20.

Cruz-Perez et al., Detection and quantitation of Aspergillus fumigatus in pure culture using polymerase chain reaction, *Molecular and Cellular Probes*, 2001; 15:81-88.

GenBank AF138288 [online] Apr. 11, 2000 [retrieved on Feb. 23, 2012] retrieved from http://www.ncbi.nlm.nih.gov/nuccore/af138288.

De Vries et al. "*Aspergillus vadensis*, a new species of the group of black Aspergilli," Antoine Van Leeuwenhoek, 2005; 87(3): 195-203.

Ahern, *The Scientist*, 1995; 20(15):1-9.

Neilsen et al., "Yeast populations associated with Ghanaian cocoa fermentations analyzed using denaturing gradient gel electrophoresis (DGGE)," *Yeast*; 2005; 22:271-284.

Bennett et al., "Mycotoxins," *Clin. Microbiol. Rev.*, 2003; 16(3):497-516.

Lee et al., J. Assoc. Off. Anal. Chem., 1989, 72(2): 345-348.

Brasel at el., Archives of Environmental Health: An international Journal, Jun. 2004, 59(6): 317-323.

Zinkevich et al., FEMSs Microbiology Ecology, 2000, 34: 147-155.

Andersson et al., Appl Environ Microbiol, 1997, 63(2): 387-393.

Quatrini et al., Hydrometallurgy, 2006, 83: 263-272.

U.S. Appl. No. 14/590,151.

U.S. Appl. No. 14/590,173.

Wulf-Durand et al., Appl. Environ. Microbiol., 1997, 63(7): 2944-2948.

Gregory et al., Toxicology Pathol., 2004, 32: 26-34.

Lee et al., J. Agric. Food Chem., 1990, 38: 444-448.

QuantiTox Kit from EviroLogix (Jul. 12, 2004).

Llobet-Brossa et al., Aquatic Microbial Ecol, 2002, 29: 211-226.

Yamanaka, Biochemistry and Environmental Biology: Chemolithoautotrophic Bacteria, 2008, pp. 7-9.

Bata et al., Appl Environ Microbiol, Mar. 1985, 49(3): 678-681.

McCormick et al., Toxins, 2011, 3: 802-814.

Willinger et al., Journal of Clinical Microbiology, 2003, 41(2): 581-585.

De Aguirre et al., Journal of Clinical Microbiology, 2004, 42(8): 3495-3504.

Hinrikson et al., Journal of Clinical Microbiology, 2005, 43(5): 2092-2103.

GenBank AF 138287 [online] Apr. 11, 2000 [retrieved Sep. 20, 2014] retrieved from http://www.ncbi.nlm.nih.gov/nuccore/af138287.

Wei et al., Anal Biochem., Feb. 1987, 160(2): 399-408.

Brasilerio et al., "Genetic variability within *Fusarium solani* specie as revealed by PCR-fingerprinting based on per markers," Brazilian Journal of Microbiology, 2004, 35: 205-210.

Suga et al., "Phylogenetic analysis of the phytopathogenic fungus *Fusarium solani* cased on the rDNA-ITS region," Mycological Research, 2000, 104(10): 1175-1183.

Haugland et al., "Identification of putative sequence specific PCR primers for detection of the toxigenic fungal species *Stachybotrys chartarum*," Mol Cell Probes, Dec. 1998, 12(6): 387-96.

Mackay et al., "Real-time PCR in the microbiology laboratory," Clin. Microbiol. Infect., 2004, 10: 190-212.

International Search Report/Written Opinion for PCT/US07/08249, dated Oct. 17, 2008.

\* cited by examiner

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tcgggggcgg ccgctgcgg                                                   19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaaagtacg tgaaattgtt g                                                21

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aagccgtgcc acattc                                                      16

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
acctagggaa tgtggctctg cg                                               22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgggccagca tcggttttg                                                   19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctagataac aagtatcgca g                                                21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
aaggcggtgt ccaagtccct tg                                              22

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcagtagcgg cgagtgaag                                                  19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agaagggcct cactgcttc                                                  19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10 tcggggtgg cctctacag                                                   19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaaaagtacg tgaaattgtt g                                               21

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aagccgtgcc acattc                                                     16

US 9,487,836 B2

METHODS AND COMPOSITIONS FOR IDENTIFYING YEAST

CROSS REFERENCE TO RELATED APPLICATIONS

This application is a continuation application of U.S. application Ser. No. 12/545,732, filed on Aug. 21, 2009, which claims priority under 35 U.S.C §119(e) to U.S. Provisional Application Ser. No. 61/091,188, filed on Aug. 22, 2008, each of which is incorporated herein by reference.

FIELD OF THE INVENTION

This invention relates to methods and compositions for detecting or identifying yeast and mycotoxins. More particularly, the invention relates to methods and compositions for detecting or identifying yeast and mycotoxins in the tissues or body fluid samples of patients.

BACKGROUND AND SUMMARY

Infections by various yeast species have become recognized as a cause of disease and ultimate death in many types of patients, including cancer patients and immunocompromised patients. Candidemia has increased over the past decade with *Candida albicans* being the most often isolated organism. Other species frequently isolated from infected patients include *Candida glabrata, Candida tropicalis*, and *Candida krusei*. Resistance to therapeutics, including the polyenes and the azoles, is common in patients infected with various yeast species.

A sensitive method using PCR assays which are based on the detection of yeast DNA in human body fluids or tissue samples is herein described. The use of realtime PCR (RT-PCR) for detection of yeast infections increases the reliability of PCR results.

In one embodiment, a method of identifying a specific yeast species in patient tissue or body fluid is provided. The method comprises the steps of extracting and recovering DNA of the yeast species from the patient tissue or body fluid, amplifying the DNA, hybridizing a probe to the DNA to specifically identify the yeast species, and specifically identifying the yeast species.

In this embodiment, 1) the amplifying step can be performed with primers that hybridize to the DNA, 2) the body fluids can be selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma, 3) the DNA can be amplified using PCR, 4) the PCR can be real-time PCR, 5) the probe can be fluorescently labeled, 6) the yeast species can be selected from the group consisting of *Candida albicans, Candida glabrata, Candida kruseii*, and *Candida tropicalis*, 7) the probe, a forward primer, and a reverse primer can be used during the amplification step and the probe comprises the sequence of SEQ ID NO: 1, the forward primer comprises the sequence of SEQ ID NO: 2, and the reverse primer comprises the sequence of SEQ ID NO: 3, 8) the probe, a forward primer, and a reverse primer can be used during the amplification step and the probe comprises the sequence of SEQ ID NO: 4, the forward primer comprises the sequence of SEQ ID NO: 5, and the reverse primer comprises the sequence of SEQ ID NO: 6, 9) the probe, a forward primer, and a reverse primer can be used during the amplification step and the probe comprises the sequence of SEQ ID NO: 7, the forward primer comprises the sequence of SEQ ID NO: 8, and the reverse primer comprises the sequence of SEQ ID NO: 9, 10) the probe, a forward primer, and a reverse primer can be used during the amplification step and the probe comprises the sequence of SEQ ID NO: 10, the forward primer comprises the sequence of SEQ ID NO: 11, and the reverse primer comprises the sequence of SEQ ID NO: 12, 11) the amplified sequence can be internal transcribed spacer regions of nuclear ribosomal DNA, and/or 12) the probe can be bound to a bead dyed with a fluorochrome. Any applicable combination of 1 through 12 is also contemplated.

In another embodiment, a method of identifying a yeast mycotoxin in patient tissue or body fluid is provided. The method comprises the steps of extracting and recovering the mycotoxin from the patient tissue or body fluid, contacting the mycotoxin with an antibody directed against the mycotoxin, and identifying the myocotoxin. In another embodiment, the method can further comprise the step of quantifying the mycotoxin. In either of these embodiments, 1) the body fluid can be selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma, 2) the mycotoxin can be selected from the group consisting of a gliotoxin and a patulin, 3) the tissue can be derived from a patient tissue biopsy and can be in a 10% formalin solution or can be in a paraffin block, and/or 4) the antibody can be bound to a bead dyed with a fluorochrome. Any applicable combination of 1 through 4 is also contemplated.

In yet another embodiment, a method of determining if a patient is at risk for or has developed a disease state related to a yeast infection is provided. The method comprises the steps of extracting and recovering a yeast mycotoxin from a tissue or body fluid of the patient, contacting the mycotoxin with an antibody directed against the toxin, identifying the mycotoxin, and determining if the patient is at risk for or has developed the disease state related to the yeast infection. In another embodiment, the method can further comprise the step of developing an effective treatment regimen for the patient.

In either of the methods in the immediately preceding paragraph, 1) the body fluid can be selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma, 2) the mycotoxin can be selected from the group consisting of a gliotoxin and a patulin, 3) the tissue can be derived from a patient tissue biopsy and can be in a 10% formalin solution or can be in a paraffin block, and/or 4) the antibody can be bound to a bead dyed with a fluorochrome. Any applicable combination of 1 through 4 is also contemplated.

In still another embodiment, a method of determining if a patient is at risk for or has developed a disease state related to a yeast infection is provided. The method comprises the steps of extracting and recovering DNA of a specific yeast species from a tissue or body fluid of the patient, amplifying the DNA, hybridizing a probe to the DNA to specifically identify the yeast species, and specifically identifying the yeast species. In another embodiment, the method can further comprise the step of developing an effective treatment regimen for the patient. In these two embodiments, the probe can be bound to a bead dyed with a fluorochrome.

In another illustrative embodiment, a kit is provided comprising a purified nucleic acid with a sequence selected from the group consisting of SEQ ID NO: 1 to SEQ ID NO: 12 or with a complement of a sequence selected from the group consisting of SEQ ID NO: 1 to SEQ ID NO: 12.

In yet another illustrative embodiment, a kit is provided comprising components for the extraction and recovery of a yeast mycotoxin from body fluid or tissue of a patient. The kit can further comprise components for identification of the mycotoxin. The components for identification of the mycotoxin can include beads dyed with a fluorochrome and coupled to antibodies to the mycotoxin or to the mycotoxin or to a mycotoxin antigen.

In another embodiment, a purified nucleic acid is provided comprising a sequence of SEQ ID NO: 1 to SEQ ID NO: 12 or a sequence that hybridizes under highly stringent conditions to a sequence consisting of SEQ ID NO: 1 to SEQ ID NO: 12.

In still another embodiment, a purified nucleic acid is provided comprising a complement of a sequence of SEQ ID NO: 1 to SEQ ID NO: 12 or a sequence that hybridizes under highly stringent conditions to a complement of a sequence consisting of SEQ ID NO: 1 to SEQ ID NO: 12.

In another aspect, a method of detecting an antibody to a mycotoxin in a patient body fluid is provided. The method comprises the steps of contacting the patient body fluid with a mycotoxin or a mycotoxin antigen coupled to a bead wherein the bead is dyed with a fluorochrome, and detecting the antibody.

In yet another aspect, a method of identifying a yeast species in a patient tissue or body fluid is provided. The method comprises the steps of identifying a yeast mycotoxin in a patient tissue or body fluid, and specifically identifying a yeast species in the mycotoxin positive patient tissue or body fluid. The method can further comprise the steps of extracting and recovering the mycotoxin from the patient tissue or body fluid, and contacting the mycotoxin with an antibody directed against the mycotoxin. The method can further comprise the steps of extracting and recovering DNA of the yeast species from the patient tissue or body fluid, amplifying the DNA, and hybridizing a probe to the DNA to specifically identify the yeast species.

In any of the embodiments in the immediately preceding paragraph, 1) the amplifying step can be performed with primers that hybridize to the DNA, 2) the body fluids can be selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma, 3) the DNA can be amplified using PCR, 4) the PCR can be real-time PCR, 5) the probe can be fluorescently labeled, 6) the yeast species can be selected from the group consisting of *Candida albicans, Candida glabrata, Candida kruseii,* and *Candida tropicalis,* 7) the amplified sequence can be internal transcribed spacer regions of nuclear ribosomal DNA, 8) the probe can be bound to a bead dyed with a fluorochrome, 9) the method can further comprise the step of quantifying the mycotoxin, 10) the mycotoxin can be selected from the group consisting of a gliotoxin and a patulin, 11) the tissue can be derived from a patient tissue biopsy and can be in a 10% formalin solution or is in a paraffin block, and/or 12) the antibody can be bound to a bead dyed with a fluorochrome. Any applicable combination of 1 through 12 is also contemplated.

DESCRIPTION OF THE ILLUSTRATIVE EMBODIMENTS

The present invention relates to methods and compositions for identifying or detecting the presence of yeast in patient tissue and body fluids. The identification and detection methods are based on 1.) amplification of yeast DNA using a PCR-based method; 2.) detection and quantification of mycotoxin in patient body fluids and tissues; and 3) combinations thereof. The methods and compositions (e.g., primers and probes) for amplification of yeast DNA are highly specific and sensitive and avoid co-amplification of or do not co-amplify non-specific human or animal nucleic acids.

The methods and compositions for detection and quantification of mycotoxins are also very specific and sensitive. These methods and compositions utilize antibody-based identification of mycotoxins. In illustrative embodiments, Enzyme Linked Immunosorbant Assay (ELISA), or affinity chromatography can be used to detect mycotoxins produced by yeast. Illustratively, the mycotoxins can be gliotoxins or patulin.

In various illustrative embodiments, body fluids that can be tested for the presence of yeast DNA or mycotoxins, or yeast DNA in combination with mycotoxins, include, but are not limited to, urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, such as seminal fluid, lymph fluid, and whole blood, serum, or plasma. These samples can be prepared for testing as described herein. In various embodiments, tissue samples can include tissue biopsies of hospital patients or out-patients and autopsy specimens. As used herein, the term "tissue" includes, but is not limited to, biopsies, autopsy specimens, cell extracts, tissue sections, aspirates, tissue swabs, and fine needle aspirates.

In accordance with the invention the word "patient" means a human or an animal, such as a domestic animal (e.g., a dog or a cat). Accordingly, the methods and compositions disclosed herein can be used for both human clinical medicine and veterinary applications. Thus, the patient afflicted with a disease state related to a yeast infection can be a human, or in the case of veterinary applications, can be a laboratory, agricultural, domestic or wild animal. The present invention can be applied to patients including, but not limited to, humans, laboratory animals such as rodents (e.g., mice, rats, hamsters, etc.), rabbits, monkeys, chimpanzees, domestic animals such as dogs, cats, and rabbits, agricultural animals such as cows, horses, pigs, sheep, goats, chickens, and wild animals in captivity such as bears, pandas, lions, tigers, leopards, elephants, zebras, giraffes, gorillas, dolphins, and whales.

The methods and compositions described herein can be used to detect or identify microbial DNA (e.g., yeast DNA) or microbial toxins (e.g., mycotoxins), or microbial DNA in combination with microbial toxins. In embodiments where the microbe is a yeast species, the microbe is typically selected from the group consisting of various *Candida* species, for example, *Candida albicans, Candida glabrata, Candida kruseii, Candida tropicalis, Candida stellatoidea, Candida parapsilosis, Candida guilliermondii, Candida viswanathii, Candida pseudotropicalis,* and *Candida lusitaniae,* as well as *Rhodotorula mucilaginosa* and *Cryptococcus neoformans.*

In one illustrative embodiment, a method is provided of identifying a specific yeast species in a patient tissue or body fluid. The method comprises the steps of extracting and recovering DNA of the yeast species from the patient tissue or body fluid, amplifying the DNA, hybridizing a probe to the DNA to specifically identify the yeast species, and specifically identifying the yeast species.

In some embodiments, real-time PCR-based methods can be used to amplify the yeast DNA and to detect and identify yeast DNA by hybridization of the probe to the yeast DNA. PCR is described in U.S. Pat. Nos. 4,683,202 and 4,800,159, incorporated herein by reference, and methods for PCR are well-known in the art. Real-time PCR combines amplification and simultaneous probe hybridization to achieve sensitive and specific detection of infectious yeast species in real-time thereby providing instant detection of the yeast species. In this embodiment, the time to detect or identify the yeast and to obtain a diagnosis is greatly reduced. Real-time PCR is conducted according to methods well-known in the art. Exemplary probes and primers and their target DNAs, that can be used in accordance with the invention are shown below. "F1" refers to a forward primer, "R1" refers to a reverse primer, and "P1" refers to a probe sequence which are well known terms in the art.

detection and identification of yeast DNA are oligonucleotides from about ten to about one hundred, more typically from about ten to about thirty or about six to about twenty-five base pairs long, but any suitable sequence length can be used. In illustrative embodiments, the primers and probes may be double-stranded or single-stranded, but the primers and probes are typically single-stranded. The primers and probes described herein are capable of specific hybridization, under appropriate hybridization conditions (e.g., appropriate buffer, ionic strength, temperature, formamide, and $MgCl_2$ concentrations), to a region of the target DNA. The primers and probes described herein are designed based on having a melting temperature within a certain range, and substantial complementarity to the target DNA. Methods for the design of primers and probes are described in Sambrook et al., "Molecular Cloning: A Laboratory Manual", 3rd Edition, Cold Spring Harbor Laboratory Press, (2001), incorporated herein by reference.

TABLE 1

Sequences and concentrations of primers and probes and corresponding probe-specific $T_m$ in real-time PCR assays

| Sequence Description | 5' Mod | Sequence | 3' Mod | Purification |
|---|---|---|---|---|
| *Candida albicans* | | | | |
| CAP1 (SEQ ID NO: 1) | 6FAM | TCGGGGGCGGCCGCTGCGG | BHQ #1 Dual | HPLC |
| CAF1 (SEQ ID NO: 2) | | AAAAAGTACGTGAAATTGTTG | | Stnd. Desalt |
| CAR1 (SEQ ID NO: 3) | | AAGCCGTGCCACATTC | | Stnd. Desalt |
| *Candida glabrata* | | | | |
| CGP1 (SEQ ID NO: 4) | 6FAM | ACCTAGGGAATGTGGCTCTGCG | BHQ #1 Dual | HPLC |
| CGF1 (SEQ ID NO: 5) | | TGGGCCAGCATCGGTTTTG | | Stnd. Desalt |
| CGR1 (SEQ ID NO: 6) | | CCTAGATAACAAGTATCGCAG | | Stnd. Desalt |
| *Candida krusei* | | | | |
| CKP1 (SEQ ID NO: 7) | 6FAM | AAGGCGGTGTCCAAGTCCCTTG | BHQ #1 Dual | HPLC |
| CKF1 (SEQ ID NO: 8) | | TCAGTAGCGGCGAGTGAAG | | Stnd. Desalt |
| CKR1 (SEQ ID NO: 9) | | AGAAGGGCCTCACTGCTTC | | Stnd. Desalt |
| *Candida tropicalis* | | | | |
| CTP1 (SEQ ID NO: 10) | 6FAM | TCGGGGGTGGCCTCTACAG | BHQ #1 Dual | HPLC |
| CTF1 (SEQ ID NO: 11) | | AAAAAGTACGTGAAATTGTTG | | Stnd. Desalt |
| CTR1 (SEQ ID NO: 12) | | AAGCCGTGCCACATTC | | Stnd. Desalt |

In various embodiments, sample preparation (i.e., preparation of the target DNA) involves rupturing the cells (e.g., cells of the tissue or yeast in patient body fluid or tissue) and isolating the yeast DNA from the lysate. Techniques for rupturing cells and for isolation of DNA are well-known in the art. For example, cells may be ruptured by using a detergent or a solvent, such as phenol-chloroform. DNA may be separated from the lysate by physical methods including, but not limited to, centrifugation, pressure techniques, or by using a substance with affinity for DNA, such as, for example, silica beads. After sufficient washing, the isolated DNA may be suspended in either water or a buffer. In other embodiments, commercial kits are available, such as Quiagen™, Nuclisensm™, and Wizard™ (Promega), and Promegam™. Methods for isolating DNA are described in Sambrook et al., "Molecular Cloning: A Laboratory Manual", 3rd Edition, Cold Spring Harbor Laboratory Press, (2001), incorporated herein by reference.

In various embodiments described herein, the primers and probes used for amplification of the target DNA and for The primers and probes described herein for use in PCR can be modified by substitution, deletion, truncation, and/or can be fused with other nucleic acid molecules wherein the resulting primers and probes hybridize specifically to the intended targets and are useful in the methods described herein for amplification of the target DNAs. Derivatives can also be made such as phosphorothioate, phosphotriester, phosphoramidate, and methylphosphonate derivatives, that specifically bind to single-stranded DNA or RNA (Goodchild, et al., Proc. Natl. Acad. Sci. 83:4143-4146 (1986)).

The invention encompasses isolated or substantially purified nucleic acids. An "isolated" or "purified" nucleic acid molecule is substantially free of other cellular material, or culture medium when produced by recombinant techniques, or substantially free of chemical precursors or other chemicals when chemically synthesized. Preferably, an "isolated" or "purified" nucleic acid is free of sequences that naturally flank the nucleic acid in the genomic DNA of the organism from which the nucleic acid is derived. For example, in various embodiments, the isolated or purified nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Also within the scope of the invention are nucleic acids complementary to the probes and primers described herein, and those that hybridize to the nucleic acids described herein or those that hybridize to their complements under highly stringent conditions. In accordance with the invention "highly stringent conditions" means hybridization at 65° C. in 5×SSPE and 50% formamide, and washing at 65° C. in 0.5×SSPE. Conditions for low stringency and moderately stringent hybridization are described in Sambrook et al., "Molecular Cloning: A Laboratory Manual", 3rd Edition, Cold Spring Harbor Laboratory Press, (2001), incorporated herein by reference. In some illustrative aspects, hybridization occurs along the full-length of the nucleic acid.

Also included are nucleic acid molecules having about 60%, about 70%, about 75%, about 80%, about 85%, about 90%, about 95%, 96%, 97%, and 98% homology to the probes and primers described herein. Determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the nucleic acid sequence of interest. Algorithms for database searching are typically based on the BLAST software (Altschul et al., 1990). In some embodiments, the percent identity can be determined along the full-length of the nucleic acid.

As used herein, the term "complementary" refers to the ability of purine and pyrimidine nucleotide sequences to associate through hydrogen bonding to form double-stranded nucleic acid molecules. Guanine and cytosine, adenine and thymine, and adenine and uracil are complementary and can associate through hydrogen bonding resulting in the formation of double-stranded nucleic acid molecules when two nucleic acid molecules have "complementary" sequences. The complementary sequences can be DNA or RNA sequences. The complementary DNA or RNA sequences are referred to as a "complement."

Techniques for synthesizing the probes and primers described herein are well-known in the art and include chemical syntheses and recombinant methods. Such techniques are described in Sambrook et al., "Molecular Cloning: A Laboratory Manual", 3rd Edition, Cold Spring Harbor Laboratory Press, (2001), incorporated herein by reference. Primers and probes can also be made commercially (e.g., CytoMol, Sunnyvale, Calif. or Integrated DNA Technologies, Skokie, Ill.). Techniques for purifying or isolating the probes and primers described herein are well-known in the art. Such techniques are described in Sambrook et al., "Molecular Cloning: A Laboratory Manual", 3rd Edition, Cold Spring Harbor Laboratory Press, (2001), incorporated herein by reference. The primers and probes described herein can be analyzed by techniques known in the art, such as restriction enzyme analysis or sequencing, to determine if the sequence of the primers and probes is correct.

In various embodiments of the methods and compositions described herein, the probes and primers can be labeled, such as with fluorescent compounds, radioactive isotopes, antigens, biotin-avidin, colorimetric compounds, or other labeling agents known to those of skill in the art, to allow detection and quantification of amplified DNA, such as by Real-Time PCR. In illustrative embodiments, the labels may include 6-carboxyfluorescein (FAM™), TET™ (tetrachloro-6-carboxyfluorescein), JOE™ (2,7,-dimethoxy-4,5-dichloro-6-carboxyfluorescein), VIC™, HEX (hexachloro-6-carboxyfluorescein), TAMRA™ (6-carboxy-N,N,N',N'-tetramethylrhodamine), BHQ™, SYBR® Green, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein, Oregon Green 488, Oregon Green 500, Oregon Green 514, Pacific Blue, REG, Rhodamine Green, Rhodamine Red, ROX, and/or Texas Red.

In one illustrative embodiment, universal probes can be used to provide a method for determining the presence of yeast DNA before conducting target-specific assays. In one embodiment, universal probes and primers can be used to detect the presence of *Candida* species.

In another illustrative embodiment, a method is provided of identifying a mycotoxin in patient tissue or body fluid. The method comprises the steps of extracting and recovering the mycotoxin from the patient tissue or body fluid, contacting the mycotoxin with an antibody directed against the mycotoxin, and identifying the myocotoxin.

In accordance with this invention, "mycotoxin" means a yeast mycotoxin, such as a gliotoxin or patulin.

Illustratively, patient (e.g., human or animal) tissue is received in 1.) a 10% formalin fluid or 2.) in a paraffin block in which the tissue has been fixed in formalin. In one embodiment for mycotoxin detection and quantitation, the tissue can then be processed by various dehydration steps and finally embedded in paraffin. In this embodiment, the tissue can then be cut in 3-5 micron samples. In an illustrative embodiment, approximately 25-35 mg of tissue can then be processed as described in Examples 2-6 for mycotoxin extraction. Illustratively, body fluids can be prepared as described in Examples 1 and 3-6 or by other methods known in the art. In another illustrative embodiment, patient body fluids can be tested for the presence of mycotoxins. Illustratively, any antigen associated with a yeast or with a mycotoxin can be detected.

In the embodiment where mycotoxins are identified and quantitated, control samples of the body fluid or tissue to be analyzed can be obtained from patients with no documented history of exposure to yeast or mycotoxins. For example, negative control samples can be obtained from autopsy specimens in which the patient had no exposure to mycotoxins or yeast (e.g., victims of motor vehicle accidents, coronary artery disease, or myocardial infarction). For positive controls, for example, samples of negative tissue and/or body fluids can be spiked with known positive amounts of mycotoxins or yeast prior to evaluation to generate a calibration curve.

In another embodiment, a method is provided of determining if a patient is at risk for or has developed a disease state related to a yeast infection. The method comprises the steps of extracting and recovering a mycotoxin (i.e., a mycotoxin or a mycotoxin antigen) from a tissue or body fluid of the patient, contacting the mycotoxin (i.e., a mycotoxin or a mycotoxin antigen) with an antibody directed against the toxin, identifying the mycotoxin (i.e., a mycotoxin or a mycotoxin antigen), and determining if the patient is at risk for or has developed the disease state related to the yeast infection. In another embodiment, a method is provided of determining if a patient is at risk for or has developed a disease state related to a yeast infection. The method comprises the steps of extracting and recovering DNA of a specific yeast species from a tissue or body fluid of the patient, amplifying the DNA, hybridizing a probe to the DNA to specifically identify the yeast species, and specifically identifying the yeast species.

In any embodiment involving "determining if the patient has developed the disease state related to the yeast infection," this phrase means "diagnosing the patient with a yeast infection."

The method embodiments described in the preceding paragraph provide methods of diagnosing yeast infections. Patients in need of diagnosis of a yeast infection can include cancer patients, post-operative patients, transplant patients, patients undergoing chemotherapy, immunosuppressed patients, and the like. Patients in need of diagnosis may include humans or animals.

In one embodiment, for diagnosing yeast infections, kits are provided. The kits are useful for identifying, detecting, or quantitating yeast DNA or mycotoxins, or yeast DNA in combination with mycotoxins, in a patient tissue or body fluid. In the embodiment where the kit is used to identify yeast DNA, the kit can contain the probes and/or primers described herein, components to extract and isolate yeast DNA, and components for DNA amplification, such as a heat stable DNA polymerase (e.g., Taq polymerase or Vent polymerase), buffers, $MgCl_2$, $H_2O$, and the like. In the embodiment where the kit is used to identify mycotoxins (i.e., a mycotoxin or a mycotoxin antigen), the kit can contain components to extract and isolate the mycotoxin (i.e., a mycotoxin or a mycotoxin antigen), antibody affinity matrices, ELISA plates, Luminex® beads, polyclonal or monoclonal antibodies, color development reagents, buffers, and the like. In one embodiment, the reagents can remain in liquid form. In another embodiment, the reagents can be lyophilized. In another illustrative embodiment, the kit can be used to detect other yeast antigens. The kits can also contain instructions for use.

In another embodiment, a kit is provided comprising a purified nucleic acid with a sequence as described in Table 1 or a complement of a sequence as described in Table 1. The kit may include a nucleic acid selected from the group consisting of SEQ ID NO: 1 to SEQ ID NO: 12, or the complement of any of these nucleic acids. "Selected from the group consisting of SEQ ID NO: 1 to SEQ ID NO: 12" means the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12. The kit can comprise components for the extraction and recovery of yeast DNA or a mycotoxin, or combinations thereof, from the body fluid or tissue of a patient. The kit can further comprise components for identification of the yeast DNA or the mycotoxin, or combinations thereof. The components for identification of the yeast DNA or the mycotoxin, or combinations thereof, can include beads dyed with a fluorochrome and coupled to a probe for the yeast DNA or to antibodies to the mycotoxin or to the mycotoxin itself or to a mycotoxin antigen.

A purified nucleic acid is also provided comprising a sequence as described in Table 1 or a sequence that hybridizes under highly stringent conditions to a sequence as described in Table 1. In accordance with the invention "highly stringent conditions" means hybridization at 65° C. in 5×SSPE and 50% formamide, and washing at 65° C. in 0.5×SSPE.

A calibration reagent (or multiple calibration reagents) can also be included in the mycotoxin kit and "calibration reagent" means any standard or reference material containing a known amount of the mycotoxin (i.e., a mycotoxin or a mycotoxin antigen). The sample suspected of containing the mycotoxin and the calibration reagent (or multiple calibration reagents) are assayed under similar conditions. The mycotoxin concentration is then calculated by comparing the results obtained for the unknown sample with the results obtained for the calibration reagent(s).

In accordance with one embodiment of the invention, a method of identifying a yeast species in a patient tissue or body fluid is described. A patient tissue or body fluid (e.g., blood, serum, spinal fluid, urine, sputum, or nasal washes) is first examined for the presence of mycotoxins. The method comprises the steps of extracting and recovering the mycotoxin from the patient tissue or body fluid, contacting the mycotoxin with an antibody directed against the mycotoxin, and identifying the mycotoxin. If a mycotoxin is present, the specimen is then tested for the presence of specific yeast species, the method further comprising the steps of extracting and recovering DNA of the yeast species from the patient tissue or body fluid, amplifying the DNA, hybridizing a probe to the DNA to specifically identify the yeast species, and specifically identifying the yeast species.

In various illustrative embodiments, the identification of a mycotoxin in a patient tissue or body fluid is followed by steps to specifically identify a corresponding yeast species in the patient tissue or body fluid. For example, if *Candida albicans, Candida glabrata, Candida kruseii,* or *Candida tropicalis* are identified in the patient tissue or body fluid, steps for specifically identifying, e.g., gliotoxins or other specific yeast mycotoxins will follow.

The following examples provide illustrative methods for carrying out the practice of the present invention. As such, these examples are provided for illustrative purposes only and are not intended to be limiting.

EXAMPLE 1

Samples

Clinical Samples

Samples obtained for routine microbiology diagnostic procedures from patients suspected and not suspected of having yeast infections were obtained for PCR assays. Samples include sputum, urine, and EDTA-anticoagulated blood. Part of the material was cultured using standard cultivation methods and part was used for RT-PCR. All specimens were stored at −20° C. until used for DNA extraction.

Yeast Strains

Yeast strains were obtained from the American Type Culture Collection (ATCC), Manassas, Va. The identification of all clinical isolates was confirmed by conventional morphological and physiological methods. DNA was extracted from the following isolates: *C. glabrata* (ATCC 90030), *C. tropicalis* (ATCC 750), *C. albicans* (ATCC 44374), and *C. krusei* (ATCC 6258).

Yeast isolates were cultured by standard cultivation methods. Cell suspensions were prepared with 0.9% saline and adjusted to a 3 McFarland standard. The yeast suspensions were centrifuged, resuspended in 200 µl 0.9% NaCl, and incubated with 20 U recombinant Lyticase (Sigma-Aldrich) at 37° C. for 30 min.

EXAMPLE 2

DNA Extraction from Blood

A modification of a protocol described by Loeffler et al. was used. For red cell lysis, 3 ml EDTA-blood was mixed with 15 ml lysis buffer (LB; 10 mM Tris [pH 7.6], 5 mM $MgCl_2$, 10 mM NaCl), incubated for 15 min on ice, and then centrifuged for 10 min at 3,000 rpm. The pellet was resuspended in 15 ml LB, incubated again for 15 mM on ice, and then centrifuged for 10 min at 3,000 rpm. For white cell lysis, the pellet was then resuspended in 1 ml LB containing 200 µg/ml protease (QIAGEN, Hilden, Germany), incubated at 65° C. for 45 min, and then centrifuged at 13,000 rpm for 10 min. To obtain spheroplasts, the pellet was resuspended in 500 µl Lyticase solution (50 mM Tris [pH 7.6], 1 mM EDTA [pH 8.0], 0.2% 2-mercaptoethanol) containing 20 U recombinant Lyticase, incubated at 37° C. for 30 min, and then centrifuged at 13,000 rpm for 10 min Finally, DNA was extracted with a High Pure PCR template preparation kit by following the instructions of the manufacturer. DNA was eluted with 100 µl elution buffer.

EXAMPLE 3

DNA Extraction from Cerebrospinal Fluid (CSF) and Sputum

For concentration of the yeast, 1 to 2 ml of the specimen was centrifuged for 5 min at 13,000 rpm. To obtain spheroplasts, the pellet plus 200 µl supernatant was incubated with 20 U recombinant Lyticase at 37° C. for 30 min. Finally, DNA was extracted with a High Pure PCR template preparation kit by following the instructions of the manufacturer. DNA was eluted with 100 µl elution buffer.

EXAMPLE 4

DNA Extraction from Tissue

Tissue (0.02 g) was incubated in 200 µl elution buffer and 200 µl binding buffer from the High Pure PCR template preparation kit with 900 µg protease at 55° C. until the tissue was completely digested. After inactivation of the protease (95° C. for 5 min), the sample was treated with 20 U recombinant Lyticase at 37° C. for 30 min to obtain spheroplasts. Finally, DNA was extracted with a High Pure PCR template preparation kit by following the instructions of the manufacturer. DNA was eluted with 100 µl elution buffer.

To avoid contamination in all extraction methods herein described, all steps were performed with aerosol-resistant tips. DNA extraction, preparation of the master mix, and addition of the template were carried out in two separate rooms. For each extraction, a reagent blank was carried out to exclude false-positive PCR results due to contamination.

EXAMPLE 5

*Candida* Extraction from Urine

*Candida* DNA was extracted from urine using a modified procedure from Norgen's Urine Bacteria Genomic DNA Isolation Kit (Thorold, ON, Canada). The kit is designed for the rapid preparation of bacterial genomic DNA from 1-20 ml of urine. The modification here demonstrates that yeast genomic DNA can be isolated from both human urine and animal urines in order to study the levels and types of yeast that are present.

Purification is based on spin column chromatography (similar to that in Quiagen's procedure listed above to extract mold spore DNA). The process involved obtaining the urine and pelleting the yeast cells present through centrifugation. The cells were then resuspended in a Resuspension Buffer and vortexed. The cells were then lysed using lysozyme, Proteinase K and a Lysis Solution. The lysate was applied to the spin columns containing resin. The resin binds DNA in a manner that depends on ionic concentrations. Thus, only the DNA will bind to the column while most of the RNA and digested proteins are removed. The bound DNA was washed twice with the two provided Wash Solutions in order to remove any impurities. Finally, the genomic DNA was eluted with the Elution Buffer. The purified DNA is of the highest quality and can be used in a number of applications. The time to complete the purification process is approximately 45 minutes.

Procedure:
1. Transfer 1.5 ml of urine to a microcentrifuge tube and centrifuge at 13,000×g for 4 minutes to pellet the cells. Pour off supernatant so as not to disturb the cell pellet.
2. Add 250 µl of Resuspension Solution (Norgen) to cell pellet and vortex gently.
3. Add 12 µl of lysozyme stock solution.
4. Add 250 µl of Lysis Solution and 12 µl of Proteinase K to the cell suspension. Mix by gentle vortexing and incubate at 55 degrees C. for 30 minutes.
5. Add 60 µl of Binding Solution to the lysate and mix by gently vortexing.
6. Assemble a micro spin column with a provided collection tube. Apply the mixture to the spin column assembly.
7. Centrifuge the unit for 3 minutes at 6000×g (8000 RPM).
8. Apply 500 µl of Wash Solution I to column, centrifuge the unit for 3 minutes at
13000×g.
9. After centrifugation, discard the flowthrough and reassemble the spin column with its collection tube.
10. Apply 500 µl of Wash Solution II to the column
11. Centrifuge for 3 minutes at 13000×g.
12. Detach the spin column from the collection tube and discard the collection tube and flow through.
13. Assemble the spin column (with DNA bound to the resin) with a 1.7 ml Elution tube.
14. Add 100 µl of Elution Buffer to the center of the resin bed.
15. Centrifuge for 1 minute at 3000 g. A portion of the Elution Buffer will pass through the column which allows for hydration of the DNA to occur.
16. Centrifuge at 13000×g for an additional 2 minutes to collect the total elution volume
17. The purified DNA can be stored at 2-8 degrees C. for 3 days or stored at −20 degrees C. for an extended amount of time.

EXAMPLE 6

Validation of *Candida* DNA

Novel real-time PCR assays targeting various yeast species, including *Candida* species (for example, *Candida albicans, Candida glabrata, Candida krusei*, and *Candida tropicalis*) are herein described. The assays can be performed either as single assays or simultaneously using a Cepheid Smart Cycler. Specimens were evaluated using pure cultures and EDTA-anticoagulated blood, cerebrospinal fluid (CSF), and urine spiked with *C. albicans, C. glabrata, C. krusei*, and *C. tropicalis* cell suspensions. Yeast Genomic DNA was isolated using NORGEN Urine Bacteria Genomic DNA Isolation Kit, Ontario Canada.

The validation showed that the Cepheid SmartCycler System utilizing specially designed target probes and primers can detect yeast in clinical fluid and urine utilizing real-time PCR technology. The validation showed that the SmartCycler can generate a qualitative determination of the presence or absence of yeast species in clinical samples for various targets, for example:

| Candida |
|---|
| C. albicans |
| C. glabrata |
| C. kruseii |
| C. tropicalis |

EXAMPLE 7

Description of Smart Cycler System

The RT-PCR assays as used herein employ a closed system using the Cepheid Smart Cycler which decreases the risk of false-positive results. Fast turnaround time is also significant in using RT-PCR. The Smart Cycler system is a real-time PCR instrument with rapid cycling times and random access capabilities. Four-color detection allows for multiplex reactions. Cepheid's single test, disposable reaction tubes were used. As testing volumes expand, the SmartCycler system can be configured for additional testing with 16, 32, 48, 64, 80, and 96 reaction site systems. The integrated software system allows for the performance of Cepheid kits or user developed assays.

The system is fully programmable and can be adapted to run the probe/primer set utilized in the targets being validated. The following represents the general flow of a clinical sample from extraction to reporting.

The clinical sample is extracted utilizing a commercial extraction kit. After the extraction, PCR reactions are setup with the extracted nucleic acid from the clinical sample (and positive and negative control) and each of the target probe and primer set. The reactions are placed in the SmartCycler and a preprogrammed real-time program is run for each reaction with data being collected by the instrument. After the instrument runs are complete, the data from each run is analyzed to determine if the run is acceptable and to determine if the clinical sample is positive or negative for the target tested. Upon completion of this analysis, a report is generated for the sample processed and the results of the testing is reviewed, approved, and reported.

A run is determined to be acceptable if the internal control for the extracted sample is positive, the positive target control is positive, the negative target control is negative, and no instrument errors are generated during the course of a PCR run.

EXAMPLE 8

Validation Protocol

Test Samples Required:

Yeast Target Samples: show that all samples can be detected utilizing target specific probes.

Yeast Target Samples: Stock suspensions of each target and serial dilutions based on the estimated concentration of the stock suspension.

| Target | 1st Point | 2nd Point | 3rd Point |
|---|---|---|---|
| | Stock | 1:10 Dil | 1:10 Dil |

Clinical Urine Samples: Negative urine samples spiked with the target and spores for the internal control Geometrica.

Negative Patient Samples: Patient urine samples expected to be negative for yeast (Used for negative controls).

Testing Conditions:

Real-time PCR was performed on the extracted target suspension stocks utilizing the Candida Assays to provide a cross over point for the stock solutions.

Real-time PCR was performed on the extracted target suspensions and the Geometrica internal control spores (dilutions shown in the chart above) with the appropriate probe/primer. PCR will also be performed on a negative tissue control for the target. The dilutions will be processed in triplicate with the target primer/probe set.

Real-time PCR was performed on the extracted target-spiked urine samples utilizing the target probe/primer set and the internal control probe/primer set. PCR will also be performed on a positive control for the target and a negative urine control for the target.

Real-time PCR was performed to show specificity from assay to assay utilizing all Candida assays run with all Candida stocks.

Data Collected:

The Real-time PCR results of the target suspension stocks.

The real-time PCR results of the extracted target suspension dilutions (run in triplicate) with the appropriate probe/primer. PCR results of a negative urine control (run in triplicate).

The real-time PCR results of the extracted target-spiked urine utilizing the target probe/primer set and the internal control probe/primer set. Also, results from the positive control for the target and a negative urine control for the target.

The real-time PCR results showing specificity from assay to assay utilizing all Candida assays with all Candida stocks.

EXAMPLE 9

Acceptance Criteria

Definitions:

Positive Result: A positive result is defined as any amplification observed crossing a baseline fluorescence of ≥30 between cycles 1 and 45 of the real-time PCR run.

Negative Result: A negative result is defined as no amplification observed crossing a baseline fluorescence of ≥30 between cycles 1 and 45 of the PCR run.

Equivocal Result: An equivocal result is defined as no amplification observed crossing a baseline fluorescence of ≥30 between cycles 1 and 45, a control out of range or questions regarding sample integrity.

Positive Control: A control that is positive for the target being tested and shows that the assay will show a positive in the presence of target DNA and that there is not PCR inhibition. (Note: a sample that shows amplification for a target when the positive control is negative can be reported as a positive result.)

Negative Control: A control that is negative for the target being tested and shows that the reagents or the sample were not contaminated with the target prior to the testing of the sample. (Note: a sample that shows amplification at an earlier cycle than a contaminated negative control can be reported as a positive due to the fact that the contamination cannot cause a sample to report a stronger positive than the contamination.)

Internal Control: A control used to show that the extraction process is working fine for the purification of nucleic acid from the clinical specimen and that a negative result is truly negative and not due to an issue associated with the extraction. (Note: the internal control must be positive for any sample to be reported as negative for a target.)

Target suspension stocks: Target stocks tested produces a positive result when run with the appropriate probe/primer set.

Target suspension Dilution and Precision: Target stocks tested produces a positive result when run with the appropriate probe/primer set for each dilution point (in triplicate) in a real-time PCR run. Results demonstrate the ability to detect each target at differing concentrations with precision in each of three reactions.

Extracted target-spiked urine samples: The spiked clinical urine sample tested produces a positive result when tested with the target probe/primer set (including the Geometrica internal control set) in a real-time PCR run. The negative control is negative, the positive control is positive, and the internal control is positive as expected.

Target Specificity: Results show that each assay is specific to the target that the assay is used to detect. This was demonstrated by running each assay with all target stocks with only the appropriate stocks giving a positive result when run with the appropriate assay.

EXAMPLE 10

Validation Results

TABLE 2

| Target Stocks | | | | | |
|---|---|---|---|---|---|
| Target | Assay # | Sample ID | MSCI Result | Result | Run Number |
| C kruseii | 1 | kruseii Stock | Positive | OK | 101007.1 |
| C tropicalis | 2 | tropicalis Stock | Positive | OK | 101007.1 |

TABLE 2-continued

| Target Stocks | | | | | |
|---|---|---|---|---|---|
| Target | Assay # | Sample ID | MSCI Result | Result | Run Number |
| C glabrata | 3 | glabrata Stock | Positive | OK | 101007.1 |
| C albicans | 4 | albicans Stock | Positive | OK | 101007.1 |

TABLE 3

| Target Detection and Precision | | | | | | |
|---|---|---|---|---|---|---|
| Target | Assay # | Load # | Stock ($1^{st}$ point) | 1:10 Dil ($2^{nd}$ Point) | 1:10 Dil ($3^{rd}$ Point) | Run Number |
| C krusei | 1 | 1 | 15.47 | 19.40 | 22.50 | 102207.3 |
| | | 2 | 15.80 | 19.24 | 22.58 | 102207.3 |
| | | 3 | 16.18 | 19.35 | na | 102207.3 |
| C tropicalis | 2 | 1 | 16.62 | 19.54 | 23.07 | 102207.3 |
| | | 2 | 16.25 | 19.74 | 22.94 | 102207.3 |
| | | 3 | 16.32 | 19.72 | na | 102207.3 |
| C glabrata | 3 | 1 | 13.78 | 17.51 | 20.76 | 102207.4 |
| | | 2 | 14.20 | 17.74 | 21.07 | 102207.4 |
| | | 3 | 14.24 | 17.75 | Na | 102207.4 |
| C albicans | 4 | 1 | 14.20 | 17.30 | 20.72 | 102207.4 |
| | | 2 | 14.10 | 17.32 | 20.54 | 102207.4 |
| | | 3 | 14.16 | 17.44 | na | 102207.4 |

TABLE 4

| Urine Samples | | | | | | | |
|---|---|---|---|---|---|---|---|
| Unknown Sample | Organism expected in Urine Samples | Assay Run | Positive Control | Negative Control | Geo | Organism Detected | |
| P3 | C albicans | C glabrata | Not Run | Not Run | Not Run | Not Run | Not Run |
| P3 | C albicans | C albicans | Positive | Negative | Positive | Positive | 102307.3 |
| P3 | C albicans | C kruseii | Not Run | Not Run | Not Run | Not Run | Not Run |
| P3 | C albicans | C tropicalis | Positive | Negative | Positive | Not Detected | 102307.2 |
| P4 | C tropicalis | C glabrata | Not Run | Not Run | Not Run | Not Run | Not Run |
| P4 | C tropicalis | C albicans | Not Run | Not Run | Not Run | Not Run | Not Run |
| P4 | C tropicalis | C kruseii | Not Run | Not Run | Not Run | Not Run | Not Run |
| P4 | C tropicalis | C tropicalis | Positive | Negative | Positive | Positive | 102307.2 |
| P5 | C kruseii | C glabrata | Not Run | Not Run | Not Run | Not Run | Not Run |
| P5 | C kruseii | C albicans | Not Run | Not Run | Not Run | Not Run | Not Run |
| P5 | C kruseii | C kruseii | Positive | Negative | Positive | Positive | 102307.2 |
| P5 | C kruseii | C tropicalis | Positive | Negative | Positive | Not Detected | 102307.2 |
| P6 | C glabrata | C glabrata | Positive | Negative | Positive | Positive | 102307.3 |
| P6 | C glabrata | C albicans | Not Run | Not Run | Not Run | Not Run | Not Run |
| P6 | C glabrata | C kruseii | Not Run | Not Run | Not Run | Not Run | Not Run |
| P6 | C glabrata | C tropicalis | Positive | Negative | Positive | Not Detected | 102307.2 |
| P9 | C albicans | C glabrata | Not Run | Not Run | Not Run | Not Run | Not Run |
| P9 | C albicans | C albicans | Positive | Negative | Positive | Positive | 102307.3 |
| P9 | C albicans | C kruseii | Not Run | Not Run | Not Run | Not Run | Not Run |
| P9 | C albicans | C tropicalis | Not Run | Not Run | Not Run | Not Run | Not Run |
| P10 | C kruseii & C glabrata | C glabrata | Positive | Negative | Positive | Positive | 102307.3 |
| P10 | C kruseii & C glabrata | C albicans | Not Run | Not Run | Not Run | Not Run | Not Run |
| P10 | C kruseii & C glabrata | C kruseii | Positive | Negative | Positive | Positive | 102307.2 |
| P10 | C kruseii & C glabrata | C tropicalis | Not Run | Not Run | Not Run | Not Run | Not Run |
| P11 | C albicans & C glabrata | C glabrata | Positive | Negative | Positive | Not detected | 102307.3 |
| P11 | C albicans & C glabrata | C albicans | Positive | Negative | Positive | Positive | 102307.3 |
| P11 | C albicans & C glabrata | C kruseii | Not Run | Not Run | Not Run | Not Run | Not Run |
| P11 | C albicans & C glabrata | C tropicalis | Not Run | Not Run | Not Run | Not Run | Not Run |
| P12 | C tropicalis (CAP PT) | C glabrata | Not Run | Not Run | Not Run | Not Run | Not Run |
| P12 | C tropicalis (CAP PT) | C albicans | Not Run | Not Run | Not Run | Not Run | Not Run |
| P12 | C tropicalis (CAP PT) | C kruseii | Not Run | Not Run | Not Run | Not Run | Not Run |
| P12 | C tropicalis (CAP PT) | C tropicalis | Positive | Negative | Positive | Positive | 102307.2 |
| P13 | Negative | C glabrata | Positive | Negative | Positive | Not Detected* | 102307.3 |

TABLE 4-continued

Urine Samples

| Unknown Sample | Organism expected in Urine Samples | Assay Run | Positive Control | Negative Control | Geo | Organism Detected | |
|---|---|---|---|---|---|---|---|
| P13 | Negative | C albicans | Positive | Negative | Positive | Not Detected* | 102307.3 |
| P13 | Negative | C kruseii | Positive | Negative | Positive | Not Detected | 102307.2 |
| P13 | Negative | C tropicalis | Positive | Negative | Positive | Not Detected* | 102307.2 |

TABLE 5

Specificity

| Sample Tested | C kruseii Assay | C albicans Assay | C tropicalis Assay | C glabrata Assay | Run Number |
|---|---|---|---|---|---|
| C kruseii (516) | Positive | Not Detected | Not Detected | Positive* | 021308.1 |
| C tropicalis (517) | Not Detected | Not Detected | Positive | Positive* | 021308.1 |
| C glabrata (518) | Not Detected | Not Detected | Not Defected | Positive | 021308.1 |
| C albicans (519) | Not Detected | Positive | Not Detected | Positive* | 021308.1 |

Four *Candida* Real-time PCR assays were run on extracted target suspension stocks. Each assay for each target was run on target solutions containing a specific organism and all assays produced positive results.

Four *Candida* Real-time PCR assays were run on extracted target suspension stocks. Each assay provided positive results for each dilution in triplicate demonstrating the ability to detect a target by differing concentrations in a precise and repetitive manner.

Four *Candida* Real-time PCR assays were run on spiked clinical urine samples. All assays were able to detect the expected targets with the exception of sample P11. Sample P11 was supposed to contain both *C. albicans* and *C. glabrata* but the assays were only able to detect *C. albicans*. Based on the overall data generated for the *C. glabrata* assay including the spiked sample number P6 and P10 it is deduced that there was either no or not adequate *C. glabrata* target present in the spiked sample number P11 to allow detection. The negative urine was negative as expected.

Four *Candida* Real-time PCR assays were tested for specificity with all assays showing great specificity with the exception of *C. glabrata*. *C. glabrata* showed some level of detection on all sample targets with the strongest detection for *C. glabrata* as expected. The weak detection of *C. glabrata* on the other three sample stocks is most likely due to some *C. glabrata* contamination in the negative urine used for the spiking experiment.

All four *Candida* assays passed the validation in exact accordance with the acceptance criteria. These four target assays can be considered validated for the qualitative determination of the presence or absence of *Candida* in clinical urine samples.

Methods and compositions, such as those for PCR, as described in WO 2008/051285, incorporated herein by reference, can also be used.

EXAMPLE 11

Detection of Yeast in Clinical Samples Utilizing Real-Time PCR Technology

PCR analysis was performed as described above using clinical samples. Specifically, urine samples from 10 patients were analyzed using PCR assays designed to target various yeast species, including *Candida albicans, Candida tropicalis, Candida glabrata,* and *Candida kruseii*.

The target probes and primers used to detect various yeast species in the urine samples utilizing real-time PCR technology were as follows:

| Candida |
|---|
| C. albicans |
| C. tropicalis |
| C. glabrata |
| C. kruseii |

Patients tested included women with asymptomatic urinary tract infections (i.e., patients with a history of recurring yeast urinary tract infections, with no present urinary complaints). All patients tested had a history of recurring yeast infections with the most common organism being *Candida albicans* (by culture history).

PCR Results:

70% of patients tested (who, at present, had no history of urinary infection) had *Candida albicans* and *Candida glabrata* present in the urine.

30% of patients tested (who, at present, had no history of urinary infection) had no findings of yeast in the urine with the four probes tested.

Typically, *Candida glabrata* is multiply resistant to many antifungal agents which are commonly used in symptomatic, culture positive urinary infections. Thus, the identification of this organism in a patient sample, will allow more powerful antifungal agents to be administered to alleviate the *C. glabrata* infection in the patient. In addition, the powerful antifungal will alleviate the other less resistant yeast species present in the urine.

The invention claimed is:

1. A method of identifying a specific yeast species in patient tissue or body fluid, the method comprising the steps of:
    extracting and recovering DNA of the yeast species from the patient tissue or body fluid;
    amplifying the DNA;
    hybridizing a probe to the DNA to specifically identify the yeast species, wherein the probe sequence consists of SEQ ID NO: 7 or a full complement of the sequence and specifically identifying the yeast species, wherein the yeast species is *Candida kruseii*.

2. The method of claim 1 wherein the amplifying step is performed with primers that hybridize to the DNA.

3. The method of claim 1 wherein the body fluids are selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma.

4. The method of claim 1 wherein the DNA is amplified using PCR.

5. The method of claim 4 wherein the PCR is real-time PCR.

6. The method of claim 1 wherein the probe is fluorescently labeled.

7. The method of claim 5 wherein the probe is fluorescently labeled.

8. The method of claim 2 wherein the probe, a forward primer, and a reverse primer are used during the amplification step and the probe comprises the sequence of SEQ ID NO: 7, the forward primer comprises the sequence of SEQ ID NO: 8, and the reverse primer comprises the sequence of SEQ ID NO: 9.

9. The method of claim 2 wherein the amplified sequence is internal transcribed spacer regions of nuclear ribosomal DNA.

10. The method of claim 1 wherein the probe is bound to a bead dyed with a fluorochrome.

11. The method of claim 1 further comprising hybridizing a probe to the DNA to specifically identify other yeast species, wherein said probe has a sequence selected from the group consisting of SEQ ID NO: 1, SEQ ID NO: 4, and SEQ ID NO: 10, or a full complement of the sequence selected from the group consisting of SEQ ID NO: 1, SEQ ID NO: 4 and SEQ ID NO: 10.

12. The method of claim 11 wherein the amplifying step is performed with primers that hybridize to the DNA.

13. The method of claim 12 wherein the probe, a forward primer, and a reverse primer are used during the amplification step and the probe comprises the sequence of SEQ ID NO: 1, the forward primer comprises the sequence of SEQ ID NO: 2, and the reverse primer comprises the sequence of SEQ ID NO: 3.

14. The method of claim 12 wherein the probe, a forward primer, and a reverse primer are used during the amplification step and the probe comprises the sequence of SEQ ID NO: 4, the forward primer comprises the sequence of SEQ ID NO: 5, and the reverse primer comprises the sequence of SEQ ID NO: 6.

15. The method of claim 12 wherein the probe, a forward primer, and a reverse primer are used during the amplification step and the probe comprises the sequence of SEQ ID NO: 10, the forward primer comprises the sequence of SEQ ID NO: 11, and the reverse primer comprises the sequence of SEQ ID NO: 12.

16. The method of claim 11, wherein the other yeast species are selected from the group consisting of *Candida albicans*, *Candida glabrata*, and *Candida tropicalis*.

17. The method of claim 11 wherein the DNA is amplified using PCR.

18. The method of claim 17 wherein the PCR is real-time PCR.

19. The method of claim 11 wherein the probe is fluorescently labeled.

* * * * *